United States Patent
Leard et al.

(10) Patent No.: US 7,812,951 B2
(45) Date of Patent: Oct. 12, 2010

(54) COLOR SENSORS USING POLARIMETRIC TECHNIQUES

(75) Inventors: Francis Lawrence Leard, Sudbury, MA (US); Nelson D. Sheppard, Milford, MA (US); Patrick J. Delaney, III, Sudbury, MA (US); Shaun Paul Hentchel, Lowell, MA (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 564 days.

(21) Appl. No.: 11/863,001

(22) Filed: Sep. 27, 2007

(65) Prior Publication Data
US 2009/0087191 A1     Apr. 2, 2009

(51) Int. Cl.
*G01J 3/51* (2006.01)
(52) U.S. Cl. .................. 356/416; 356/425
(58) Field of Classification Search .......... 356/402, 356/416
See application file for complete search history.

(56) References Cited

U.S. PATENT DOCUMENTS 4,699,510 A * 10/1987 Alguard ............... 356/73

* cited by examiner

*Primary Examiner*—F. L Evans
(74) *Attorney, Agent, or Firm*—Schwegman Lundberg et al.; William R. Walbrun; John M. Miller

(57) ABSTRACT

Embodiments include an apparatus including a color sensor including a transmitter portion and a receiver portion, the transmitter portion including a light source operable to generate and transmit a light having a particular range of wavelengths, the receiver portion including a first detector operable to receive a first portion of the light emitted from the transmitter portion and to measure a luminance of the received first portion of the emitted light, and a second detector including a polarization filter, the second detector operable to receive a second portion of the light emitted from the transmitter after the second portion has passed through the polarization filter, and operable to measure a pure color of the received second portion of transmitted light.

20 Claims, 6 Drawing Sheets

COLOR SENSORS USING POLARIMETRIC TECHNIQUES

FIELD OF THE INVENTION

The present invention relates generally to color sensing and color sensors.

BACKGROUND

Often, the presence or absence of color, or the presence or absence of a particular color, will indicate a quality level associated with a product, including a quality level or a characteristic associated with the colors of a solid object or a fluid. The ability to detect and classify by color in a manufacturing or assembly operation is a useful tool in assuring quality and in speeding production rates. Electrical devices, such as color sensors, that are operable to perform color sensing are valuable tools in testing, manufacturing, and assembly operations. Color sensors may be used for color monitoring functions in operations involving the production of products such as paint and textiles, and in color printing applications, where color control is a critical measure of quality in the produced product. In the food industry, color sensing is important to assure visual appeal of the product, such a color of a drink packaged in a transparent container, and may be used to detect contamination or other health related issues in food and beverage goods intended for human consumption. In addition, color sensors are often employed as an important part of medical processes and diagnostic testing, for example, in color sensing used in blood diagnostics, urine analysis, and color matching in dental applications.

SUMMARY

The apparatus, methods, and systems of the various embodiments of the present inventive subject matter will be understood by reading and studying the following specification.

Various embodiments include an apparatus including a color sensor including a transmitter portion and a receiver portion, the transmitter portion including a light source operable to generate and transmit a light having a particular range of wavelengths, the receiver portion including a first detector operable to receive a first portion of the light emitted from the transmitter portion and to measure a luminance of the received first portion of the emitted light, and a second detector including a polarization filter, the second detector operable to receive a second portion of the light emitted from the transmitter after the second portion has passed through the polarization filter, and operable to measure a pure color of the received second portion of transmitted light.

Various embodiments include a method comprising generating a light having a known range of wavelengths, applying the generated light to a target object, the target object including a color of the target object to be quantified, receiving at a first detector a first portion of the generated light after applying the generated light to the target object, generating an output representative of a luminescence value of the portion of the light received at the first detector, receiving at a polarization filter the first portion of the generated light after applying the generated light to the target object, passing a second portion of the first portion of the generated light through the polarization filter, and then receiving at a second detector the portion of the light that has passed through the polarization filter, and generating an output representative of a pure color value for the portion of the light received at the second detector.

Various embodiments include a system comprising a color sensor including a transmitter portion and a receiver portion, wherein the transmitter portion including a light source operable to emit a light having a particular range of wavelengths, the receiver portion including a first detector operable to receive a reflected portion of the light emitted from the transmitter portion after the emitted light is reflected off a surface of a target object, and to measure a luminance of the received reflected portion of the emitted light, and a second detector including a color-specific filter, the second detector operable to receive the reflected portion of the light emitted from the portion of the light emitted from a the transmitter portion after the second portion has passed through the color specific filter, and operable to measure a pure color of the received second portion of emitted light, a sensing position located proximal to the color sensor and at a distance from the color sensor wherein the transmitter portion is operable to transmit a light from the light source and have the transmitted light incident on an object present at the sensing position and wherein the light incident on the object reflects off a surface of the object to generate the reflected portion of the light, and a mechanism operable to place the object into the sensing position and to remove the object from the sensing position.

These and other aspects, embodiments, advantages, and features will become apparent from the following description and the referenced drawings.

DETAILED DESCRIPTION

Figure 1:
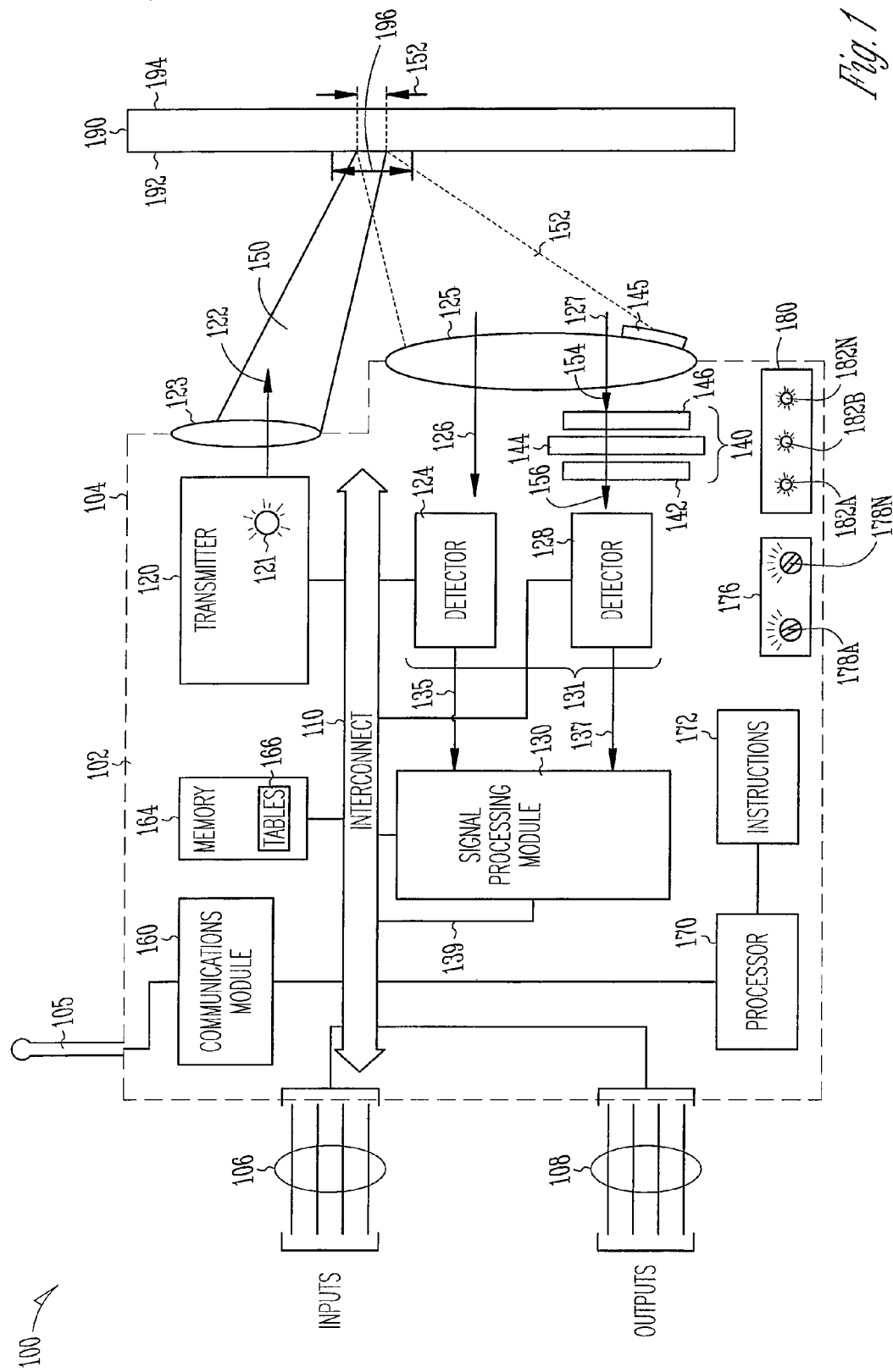
FIG. 1 illustrates a functional block diagram of a color sensor according to various embodiments.

In the following detailed description of the embodiments of the inventive subject matter, reference is made to the accompanying drawings that form a part hereof, and in which are shown by way of illustration, specific embodiments in which the inventive subject matter may be practiced. These embodiments are described in sufficient detail to enable those skilled in the art to practice the present invention. Other embodiments may be utilized and structural, logical, and electrical changes may be made without departing from the scope of the invention. The various embodiments disclosed herein are not necessarily mutually exclusive, as some embodiments can be combined with one or more other embodiments to form new embodiments. The following detailed description is, therefore, not to be taken in a limiting sense.

Various embodiments described herein include a color sensor having a transmitter operable as a source to generate a light, and two detectors operable to detect the generated light. In various embodiments, one detector measures luminance, while the other measures pure color. In various embodiments, a color-specific filter is placed so that light passes through the color-specific filter before reaching the detector measuring pure color, and so that the light does not pass through the color-specific filter before reaching the detector measuring luminance. In various embodiments, the color-specific filter consists of a half-wave plate sandwiched between two crossed polarizer layers.

Generally, a polarizer is a device that converts an unpolarized or mixed-polarization beam of electromagnetic waves into a beam with a single polarization state, usually a single linear polarization. In various embodiments the polarizer layers of the color-specific filter each act as a polarizer operable to polarize any light passing through polarizer layer of the color-specific filter.

Generally, a wave plate, sometimes referred to as a "retarder," is an optical device that alters the polarization state of a light wave traveling through it. A wave plate works by shifting the phase of the light wave between two perpendicular polarization components. A wave plate is characterized by the amount of relative phase $\Gamma$ that it imparts on the two components, which is related to the birefringence $\Delta n$ and the thickness L of the crystal by the formula $$\Gamma = 2\pi \Delta n L / \lambda.$$

A quarter-wave plate imparts a quarter wavelength phase shift on the light passing through the quarter-wave plate, and thus changes linearly polarized light to circular, and vice versa. This is done by adjusting the plane of the incident light on the quarter-wave plate so that it provides a 45 degree angle with the fast axis.

A half-wave plate retards one polarization of the light passing through the half-wave plate by a half wavelength, or 180 degrees. This type of waveplate rotates the polarization direction of linear polarized light.

Because of dispersion, a simple wave plate will impart a phase difference that depends on the wavelength of the light. Wave plates are thus manufactured to work for a particular range of wavelengths.

In various embodiments, the wave plate of the color-specific filter included in the color sensor is a half-wave plate located between two polarizer layers, wherein the two polarizer layers are crossed polarization layer having their respective axis of polarization at 90 degrees to one and other. In various embodiments, the half-wave plate is a wavelength dependent structure that is set up at 45 degrees with respect to either polarizer layer.

In various embodiments, the color sensor including the color-specific filter is used to quantify a color of an object, including but not limited to a color on a surface of an opaque object. In various embodiments, the color sensor is used to quantify a color of a translucent or transparent object, such as a liquid, a gas, or a solid such as plastic or glass.

In operation, the transmitter of the color sensor generates a light to be directed to the object, which may be referred to as the "target object." In various embodiments, the generated light is a true "white" light including light across the entire spectrum of visible light. Generally, visible light is considered to be light having wavelengths from about 380 nanometers to about 750 nanometers. In various embodiments, a spectrum of white light may have wavelengths over a smaller range or over a larger range of wavelengths as compared to the 380-750 nanometer range.

In addition, embodiments are not limited to color sensors having transmitters generating true white light. In various embodiments, the transmitter generates light in the ultraviolet range. Ultraviolet light is not necessarily restricted to a particular range of wavelengths. In various embodiments, ultraviolet light is considered to be light having wavelengths in the range of 200 and 400 nanometers. In various embodiments, ultraviolet light is considered to include light having wavelengths less than 280 nanometers.

In various embodiments, the transmitter generates light in the infrared range. Infrared light is not necessarily restricted to a particular range of wavelengths. In various embodiments, infrared light is considered to be light having wavelengths in the range of 0.7 to 350 micrometers.

In various embodiments, the color-specific filter is designed to pass the wavelengths, with various degrees of retardation, the specific wavelengths of light generated by the transmitter of the same color sensor in which the color-specific filter is installed. Thus, the filter is referred to as "color-specific" in that the filter is designed to provide a specific response with regard to the amount of retardation experienced by each of the different wavelengths of light within the range of specific wavelengths of light generated by the transmitter of the same color sensor in which the color-specific filter is installed. Response refers to the amount of attenuation of intensity experienced by each of the particular wavelengths of light passing through the color-specific filter.

In various embodiments, transmitting the light generated by the transmitter refers to directing the light from the transmitter to the target object. In various embodiments, at least part of the transmission occurs through open and ambient air surrounding the target object. In various embodiments, transmitting the light includes using a lens to focus or otherwise direct the light. In various embodiments, some of the transmission path for the light moving between the transmitter and the target object includes a path or channel other than open and ambient air, such as a fiber optic cable or a light pipe.

In various embodiments, upon reaching the target object, at least some of the light from the transmitter is reflected back (or transmitted through in the case of a translucent or transparent target object), and is directed back to the two detectors of the color sensor that initially provided the light. In various embodiments, the some portion of the returning light reaches the detector measuring luminance without passing through a color-specific filter, and a measurement of the luminance is made. The same portion of the returning light is also passed though the color-specific filter. In passing through the color-specific filter, the intensity of the wavelengths reaching the color-specific filter are mapped to a gray scale, allowing the pure color detector receiving this returning light, after the returning light has passed through the color-specific filter, to measure the intensity of each wavelength included in the returning and filtered light. The measurements taken by each of the two detectors are processed to quantify a color or colors, as further described herein.

Thus, embodiments of the color sensor of the present inventive subject matter use an artifact of color, that is, different wavelengths of light, to determine color and luminance that can be used to measure a gray scale level of a pure color, an artifact not being captured by currently available color sensors. The measurement of both the luminance and the pure color is important. If the color to be quantified and associated with the target object is a metameric color, that is, one that produces a same response via color rationing as the desired color, then the previously available sensors will be fooled by such as response. The embodiments of the color sensor of the present inventive subject matter, by using the luminance change along with the pure color channel, are operable to differentiate the metameric color as different from the expected or proper color of the target object being tested.

In a case where the color being quantified on the target object is partially obscured, dirty, or otherwise tainted, the previously available color sensors may also be fooled. The embodiments of the color sensor of the present inventive subject matter will not be fooled, as the additional information provided by the luminance channel allows the color sensor of the present inventive subject matter to properly quantify the partially obscure, dirty or otherwise tainted color associated with the target object.

The various embodiments of inventive color sensor described herein are operable to quantify colors over a complete and wide range of visible colors, and are operable to distinguish multiple colors within this range using just one filter and two detectors. Various embodiments are operable to distinguish multiple colors within other ranges of wavelengths, including wavelengths in the infrared and ultraviolet ranges. Thus, a user having a need for a variety of color sensing applications including various and different ranges of colors can use a same generic color sensor for all these applications, and thus realize a cost reduction in maintaining a smaller inventory of spare parts. Further, cost savings are realized in that using this same generic color sensor for multiple color sensing operations reduces the need to learn how to use and apply different color sensors for a large variety of color sensing applications. Further, embodiments of the present inventive color sensor can be designed to employ standard and commercially available detectors for each of the luminance measurements and the pure color measurements. Use of standard and commercially available detectors further reduces the overall cost of each of the inventive color sensors by eliminating the need to design and produce custom detectors.

FIG. 1 illustrates a functional block diagram 100 of a color sensor 102 according to various embodiments. Diagram 100 includes a color sensor 102 including a transmitter portion including a transmitter 120, and a receiver portion 131 including a first detector 124 and a second detector 128. In various embodiments, color sensor 102 includes a housing 104 that includes transmitter 120 and receiver portion 131. In various embodiments, housing 104 includes any combination of the additional devices included in color sensor 102 as shown in FIG. 1. These other devices include any combination of a signal processing module 130, processor 170, instructions 172, memory 164, and communications module 160.

In various embodiments, any combination of devices including transmitter 120, receiver portion 131, signal processing module 130, processor 170, instructions 172, memory 164, and communications module 160 include any combination of these devices coupled to an interconnect 110. Interconnect 110 is not limited to any particular type or types of interconnect, and may include any type or types of connections or couplings operable to provide electrical and communicative couplings between the various devices included in color sensor 102. Interconnect 110 in various embodiments includes, but is not limited to, any one or more types of interconnects including physical conductors such as wires, and such as traces on a substrate or a circuit board, bus lines, and transmission lines. Communications over interconnect 110 are not limited to any particular type or protocol of communications, and may include any of one or more formats and protocols operable to provide communications between various devices in color sensor 102.

In various embodiments, transmitter 120 is operable to generate a light 122, as represented by the arrow associated with reference number 122. The light 122 generated by transmitter 120 is not limited to any particular means of generating the light. In various embodiments, light 122 is generated by a light emitting diode (LED) 121. In various embodiments, light emitting diode 121 is a white light LED including a gallium nitride (GaN) LED source and a phosphor encapsulate that creates a white light source. In various embodiments, light 122 includes wavelengths of light associated with ultraviolet light. In various embodiments, light 122 includes wavelengths of light associated with infrared light.

In various embodiments, transmitter 120 is located adjacent to light transmission device 123, wherein light transmission device 123 is physically located so that the light generated by transmitter 120 will be directed to pass through light transmission device 123, as represented by the arrow associated with reference number 122. Light transmission device 123 is not limited to any particular type of device, and includes any device that is operable to transmit the wavelengths of light generated by transmitter 120. In various embodiments, light transmission device 123 is a lens. In various embodiments, light transmission device 123 is made of clear glass, or a clear plastic material. In various embodiments, light transmission device 123 is a fiber optic material operable to transmit light along and through the fiber optical material.

In various embodiments, light transmission device 123 is operable to focus the light generated by transmitter 120 into a beam 150 directed to a focal area 196 on a surface 192 of a target object 190. In various embodiments, target object 190 is any object on which a color calibration, color testing, or color verification operation is to be performed. Any of these operations are included in and are referred to as color sensing operations. In various embodiments, color calibration includes operations used to calibrate the color sensor 102. In various embodiments, color testing includes teaching the color sensor 102 a color or a range of colors associated with target object 190, which in some embodiments, includes target object 190 being a "standard" having a known and desired color or range of colors for a given color sensing operation or product. In various embodiments, color verification includes performing a color sensing operation on target object 190 to determine if a color associated with target object 190 conforms to an expected or desired color or range of colors. In various embodiments color verification includes providing an output from color sensor 102 indicative of whether or not a color verification operation performed on target object 190 resulted in the color or range of colors of target object 190 complying with the expected or desired color or range of colors.

Generally, target object 190 is not part of color sensor 102. However, target object 190 may be an object used in a calibration of color sensor 102, wherein target object 190 has a known color at surface 192 within focal area 196, and is intended to provide a known light response to the receiver portion 131 of color sensor 102 when receiving light 122 for the purposes of testing or calibrating color sensor 102.

In various embodiments, focal area 196 of target object 190 includes a color at surface 192 that is being quantified using color sensor 102. In various embodiments, target object 190 is opaque, and the color on surface 192 is the parameter being quantified. In various embodiments, target object 190 is either translucent or transparent, and a color or colors of target object 190 between surfaces 192 and 194 are the parameters that are being quantified, as is further described by way of illustration with respect to FIG. 3C.

Referring back to FIG. 1, in various embodiments target object 190 is positioned relative to color sensor 102 so that light from beam 150 is incident on surface 192 and has some portion of the light reflected back to the receiver portion 131 of color sensor 102. In various embodiments, the some portion of the light reflected back is represented by beam 152, and includes wavelengths of light that have less intensity, or are completely missing, from beam 152 and that were present in the light of beam 150. The changes in wavelengths and intensity of wavelength between beam 150 and beam 152 are caused by the rates of absorption and rates and angles of reflections of the light in beam 150 at surface 192 and within focal area 196, due at least in part to the color at surface 192 in focal area 196.

In various embodiments, some portion of beam 152 is directed to first detector 124, as represented by arrow 126, and some portion of beam 152, as generally indicated by the arrow 127, is directed to pass through polarization filter 140, as represented by arrow 156, and then is directed to second detector 128.

In various embodiments, detector 124 is a detector operable to measure luminance of beam 152. In various embodiments, polarization filter 140 includes a wave plate 144 between a first polarizer layer 146 and a second polarizer layer 142. In various embodiments, polarization filter 140 is operable to retard any different wavelengths present in the light of beam 150 by different amounts, providing a grey scale of intensity for every wavelength potentially included in the light of beam 152 based on the known wavelengths of light being provided in the light of beam 150. The light passing through polarization filter 140 is received at second detector 128. In various embodiments, detector 128 is operable to determine pure color, by detecting the intensity level of each wavelength of the filtered light received at detector 128.

In various embodiments, light transmission device 125 is operable to receive beam 152, and to direct the light included in beam 152 to polarization filter 140, as represented by the arrowhead 154. Although shown as a single device in FIG. 1, in various embodiments light transmission device 125 includes separate light transmission devices to direct beam 152 to first detector 124 and to polarization filter 140 respectively. In various embodiments, light transmission device 125 is a lens. In various embodiments, light transmission device 125 includes a first lens to direct light to detector 124, and a second lens to direct light to polarization filter 140. In various embodiments, light transmission device 125 includes a fiber optic cable or a light pipe. Light transmission device 125 is not limited to any particular type of material. In various embodiments, light transmission device 125 is formed of a clear glass. In various embodiments, light transmission device 125 is formed of clear plastic.

Polarization filter 140 is not limited to being located behind light transmission device 125 as shown in FIG. 1. Polarization filter 140 can be located in any portion of color sensor 102 so that light from beam 152 passes through polarization filter 140 before reaching detector 128. In various embodiments, polarization filter 140 is included in light transmission device 125. In various embodiment, polarization filter 140 is included as a surface 145 of light transmission device 125.

In various embodiments, color sensor 102 includes a signal processing module 130. Signal processing module 130 is not limited to any particular type of signal processing module, and may include hardware, software, or a combination of hardware and software operable to provide signal processing functions. In various embodiments, signal processing module 130 receives an output signal from an output 135 of the first detector 124 and an output signal from an output 137 of second detector 128. Signal processing module 130 is operable to provide signal processing on the signals received from first detector 124 and second detector 128, and to provide an output 139.

In various embodiments, the output signal from output 135 of the first detector includes a value representative of a mean value for the luminance of the light received at the first detector. In various embodiments, the output 135 of the first detector 124 is a voltage representing the mean value of the light received at the first detector. In various embodiments, the output signal 137 of the second detector includes a value representative of a mean value for the luminance of the light received at the second detector. In various embodiments, the output 137 of the second detector 128 is a voltage representing the mean value of the light received at the second detector.

In various embodiments, output 139 represents an output signal provided by the signal processing module 130 and is based on the input signals received from the first and the second detectors. Output 139 is not limited to any particular type of output signal. In various embodiments, output signal 139 is an analog output signal including a voltage representative of one or more values provided by signal processing module 130. In various embodiments, output signal 139 is a stream of digital data representative of one or more values provided by signal processing module 130. In various embodiments, signal processing module 130 provides an output signal at output 139 having a value representative of a ratio of the values received from outputs 135 and 137. In various embodiments, signal processing module 130 is operable to sample output 135 and 137 at a sampling rate, or at different sampling rates for output 135 versus output 137, and to provide an output signal, or in some embodiments, a series of output signals, each output signal having a value determined by any combination of the sampled outputs from output 135 and output 137.

Output 139 is not limited to providing any particular type of output signal at output 139, and is operable to provide any type of output signal used to provide information related to the actual quantities or to some type of relationship between the output signal 135 from detector 124 and the output signal 137 from detector 128.

In various embodiments, color sensor 102 includes a processor 170. Processor 170 is not limited to any particular type of processor, and in various embodiments, is a custom processor specifically designed for use in color sensor 102. In various embodiments, instructions 172 are stored in a memory device and coupled to processor 170. Instructions 172 include instructions used by processor 170 in order to perform any one or more of the operations controlled by processor 170. In various embodiments, processor 170 is operable to control transmitter 120 and first detector 124 and second detector 128 in color sensing operations. In various embodiments, processor 170 is operable to control signal processing module 130 in any signal processing operations performed at signal processing module 130.

In various embodiments, processor 170 is operable to control memory operations including memory 164, including operations involving storing values into tables 166, and retrieving values stored in tables 166. In various embodiments, processor 170 controls communications operations involving communications module 160. Communications operations include receiving signals at communications module 160 over antenna 105, and transmitting signals from color sensor 102 through antenna 105. Through communications module 160 and antenna 105, color sensor 102 in various embodiments includes a wireless connection to a tracking system (not shown in FIG. 1) to communication signals between color sensor 102 and the tracking system.

In various embodiments, processor 170 is operable to determine a setting of input controls 176, and to control the operations of color sensor 102 based on the setting of any one or more of input controls 176. Input controls 176 are not limited to a particular number or type of input controls, and may include any number of individual input controls as represented by reference numbers 178A-N. Input controls 176 in various embodiments include rotary switches or variable resistors operable to allow an input setting to be made to color sensor 102 by adjusting a given one of the rotary switches or variable resistors. Input controls 176 are not limited to any particular type of inputs. In various embodiments, input controls 176 include one or more switches used to provide inputs and parameters settings for color sensor 102 by setting the position or positions of the one or more switches. In controls 176 can include any type of input to color sensing, including but not limited to setting a sensitivity, adjusting the focal range, and selecting a mode of operation related to color sensor 102.

In various embodiments, processor 170 is operableable to provide output signals to control a status indication of any one or more of output indicators 180. In various embodiments, an output signal for any one or more of output indicators 180 turns on a given one of status indicators 182A-N. Status indicators 182A-N are not limited to any particular type of status indicators. In various embodiments, one or more of status indicators include a light emitting diode. In various embodiments, an output signal for any given one of output indicators 180 includes turning the given output indicator to be steadily "on". In various embodiments, an output signal for any given one of output indicators 180 causes the given output indicator to flash "on" and "off" at some rate. In various embodiments, the rate at which a given output indicator flashes is representative of some parameter related to color sensor 102 or to a color sensing operation being performed by color sensor 102, as being indicated by the given output indicator.

In various embodiments, color sensor 102 includes one or more inputs 106. Inputs 106 are not limited to any particular type of inputs. In various embodiments, inputs 106 include one or more inputs for providing electrical power to color sensor 102. By way of illustration, in various embodiments, color sensor 102 is powered using a direct current power that is provided by conductors included in inputs 106. In various embodiments, inputs 106 includes a signal line input operable to trigger a color test. In various embodiments, inputs 106 include one or more signal line inputs operable to provide data to color sensor 102. In various embodiments, the data provided to color sensor 102 includes data stored in tables 166. In various embodiments, the data includes data related to values associated with color or ranges of colors that are to be the expected or desired colors and ranges of colors associated with color sensing operations to be performed by the color sensor 102.

In operation, a color sensing operation is initiated at color sensor 102. In various embodiments, the color sensing operation is initiated by a signal received at color sensor 102. In various embodiments, the signal to initiate a color sensing operation is received as a trigger signal through inputs 106, or as a signal received at antenna 105. Upon initiation, transmitter 120 generates and transmits a light 122. Light 122 is directed as a beam 150 to target object 190, and is reflected back (or in the instances of a translucent or transparent object, is directed back) to detector 124 and polarization filter 140 as beam 152. Detector 124 provides as an output signal 135 an output representative of a measurement of the luminance value of the light received at detector 124 as provided in beam 152. Light from beam 152 that is received at polarization filter 140 passes through and is filtered by polarization filter 140, and is then directed to detector 128. Detector 128 provides as an output signal 137, an output representative of a measurement of the pure color or colors of the wavelengths of light received at detector 128.

The output signals from detector 124 and detector 128 are processed through signal processing module 130 to provide an output 139. Output 139 includes one or more values that can be used to verify whether the color or colors sensed during the color sensing operation and associated with the target object 190 fall within an expected or desired range of color or colors. In various embodiments, an output signal is provided indicating that the color sensing operation is completed. In various embodiments, an output signal is provided indicating a status associated with color sensing operation, including but not limited to a status of "pass" or "fail" associated with the results obtained from the color sensing operation.

In various embodiments, a signal indicating that the color sensing operation is complete is provided as an output from color sensor 102 on one or more lines included in output 108. In various embodiments, a signal indicating a status associated with the results of a color sensing operation is provided as an output from color sensor 102 on one or more lines included in output 108. In various embodiments, either or both of these signals are provided as output signals transmitted from antenna 105 of color sensor 102. In various embodiments, a given one of status indicators 182A-N provides an output indicative of whether or not a sensing operator is completed. In various embodiments, a given one of status indicators 182A-N provides an output indicative of a status associated with a completed color sensing operation.

Figure 2A:
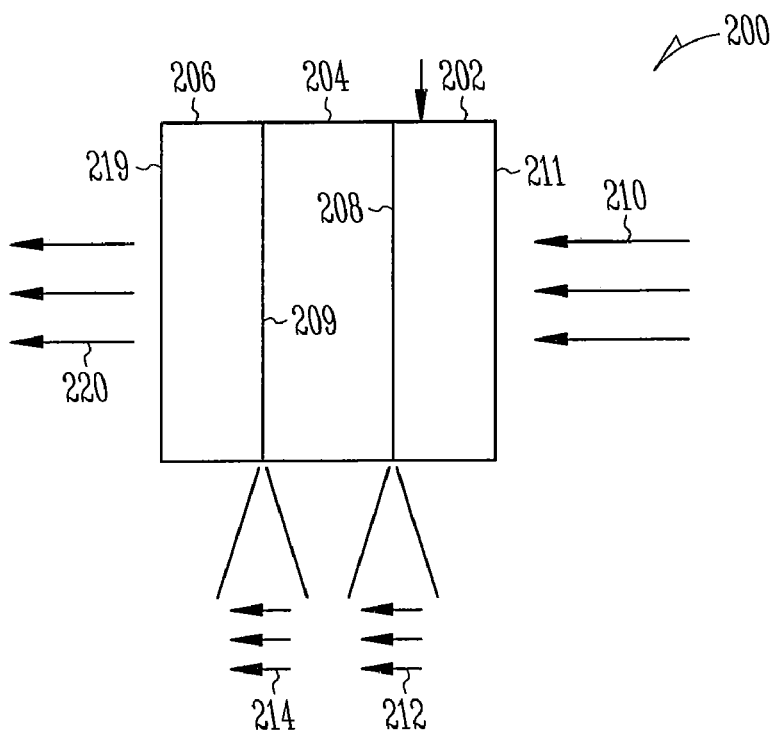
FIG. 2A illustrates a polarization filter according to various embodiments.

FIG. 2A illustrates a polarization filter 200 according to various embodiments. In various embodiments, polarization filter 200 is the color-specific filter 140 as shown in FIG. 1. Polarization filter 200 includes a first polarizer layer 202 adjacent to a wave plate 204, and a second polarizer layer 206 adjacent to wave plate 204 and on an opposite side of wave plate 204 as the first polarizer layer 202. In various embodiments, wave plate 204 includes a first surface 208 and a second surface 209. In various embodiments, first polarizer layer 202 is directly in contact with the first surface 208, and the second polarizer layer 206 is directly in contact with second surface 209. In various embodiments, the first polarizer layer 202 is adjacent to but not in direct contact with first surface 208. In various embodiments, second polarizer layer 206 is adjacent to but not in direct contact with second surface 209.

In various embodiments, first polarizer layer 202, wave plate 204, and second polarizer layer 206 are arranged as cross polarization layers, wherein the axis of polarization for first polarizer layer 202 is arranged to be co-planner and rotated 90 degrees relative to the axis of polarization of the second polarizer layer 206.

In various embodiments, wave plate 204 is a half wave plate. Wave plate 204 is not limited to any particular type of wave plate.

Polarization filter 200 is not limited to a particular type of polarization filter. In various embodiments, polarization filter 200 is a thin film based polarization filter. In various embodiments, polarization filter 200 is a plasmonic based polarization filter. In various embodiments, polarization filter 200 is a resonant based polarization filter. In various embodiments, polarization filter 200 is a dye based polarization filter. In various embodiments, polarization filter 200 is a sub-wavelength grating based polarization filter.

In operation, unpolarized light 210 becomes incident on polarization filter 200 at surface 211 of the first polarizer layer 202. In various embodiments, unpolarized light 210 is the portion of a generated and transmitted light from a color sensor, such as color sensor 102, that has been reflected off a surface of a target object, such as beam 152 as shown in FIG. 1. In various embodiments, unpolarized light 210 is the portion of generated and transmitted light from a color sensor, such as color sensor 102, that has been transmitted through a translucent or transparent target object, as further described with respect to FIG. 3B.

Referring again to FIG. 2A, unpolarized light 210 passes through first polarizer layer 202, resulting in a light 212. In various embodiments, light 212 is a linearly polarized light. Light 212 arrives at first surface 208, passes through wave plate 204, resulting in light 214 at second surface 209. In various embodiments, light 214 includes an elliptically polarized light. In various embodiments, wave plate 204 has a 45 degree orientation relative to resolve wavelengths along both the fast axis and the slow axis of the wave plate 204. Light 214 leaves wave plate 204 and passes through second polarizer layer 206, resulting in light 220 exiting surface 219 of polarization filter 200. In various embodiments, light 220 includes polarized light having an intensity that has been reduced for certain wavelengths and in proportion to the wavelength of light provided in the unpolarized light 210.

In various embodiments, polarization filter 200 is designed to be "full on" for wavelengths of light near the ultra-violet wavelengths but still in the visible range of light, and is "full off" for wavelengths of light near the infra-red wavelengths but still in the visible range of light. Such a design for polarization filter 200 is employed when the light incident on polarization filter 200 as unpolarized light 210 is provided as reflected light from a target object having the reflected light generated by a transmitter providing a source of white light including wavelengths over the entire visible spectrum of light.

In various embodiments, polarization filter 200 is designed to attenuate unpolarized light 210 based on wavelength over a range of light other than visible light. In various embodiments, polarization filter 200 is designed to attenuate unpolarized light 210 to provide light 220 over a range of wavelengths of light included in ultraviolet light. In various embodiments, polarization filter 200 is designed to attenuate unpolarized light 210 based on wavelengths to provide light 220 over a range of wavelengths of light in the infrared light range.

Figure 2B:
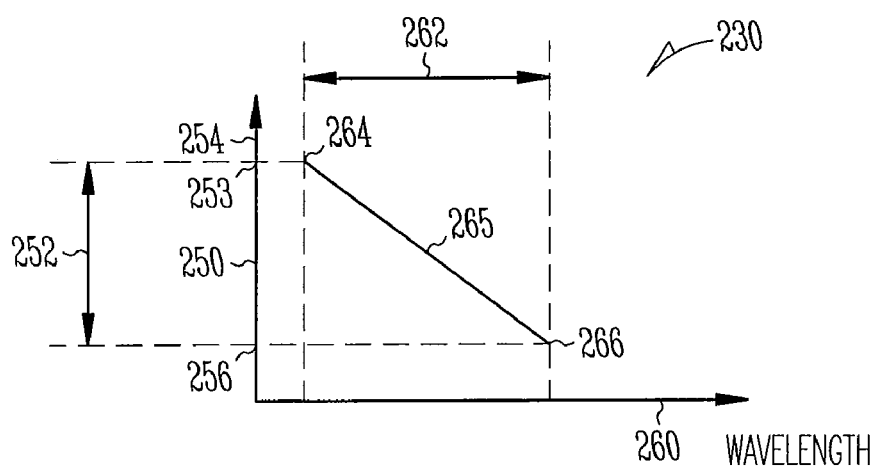
FIG. 2B illustrates a graph of retardation versus wavelength of light according to various embodiments.

FIG. 2B illustrates a graph 230 of retardation versus wavelength of light passing through a polarization filter, such as polarization filter 200, according to various embodiments. Graph 230 includes vertical axis 254 indicative of retardation of light passing through polarization filter 200, and includes a horizontal axis 260 representing wavelengths of light passing through polarization filter 200. In various embodiments, range 262 represents a range of wavelengths of light, the shortest wavelength at wavelength 264, and the longest wavelength at wavelength 266. In various embodiments, range 262 represents the range of visible light as would be included in a true white light, having wavelength 264 at about 400 nM, and a wavelength 266 at about 700 nM. In various embodiments, range 262 represents the range of true while light generated by a light transmitted from LED 121 of transmitter 120 in FIG. 1.

Referring again to FIG. 2B, curve 265 represents the relative levels of retardation of light passing through polarization filter 200 for the given wavelengths within range 262. At wavelength 264, any light at the wavelength 264 passing through polarization filter 200 will experience a retardation of almost none, as represented by retardation level 253. At wavelength 266, any light passing through polarization filter 200 will experience a retardation of nearly 100 percent, as represented by retardation level 256. Light having wavelengths within range 262 and between wavelengths 264 and 266 will experience a retardation level represented by retardation range 252 along curve 265.

In various embodiments, curve 265 is approximately a straight line. By providing the retardation curve 265, polarization filter 200 is operable to provide a grey scaling of a range of light having wavelengths within range 262 and including wavelengths 264 and 266.

Figure 2C:
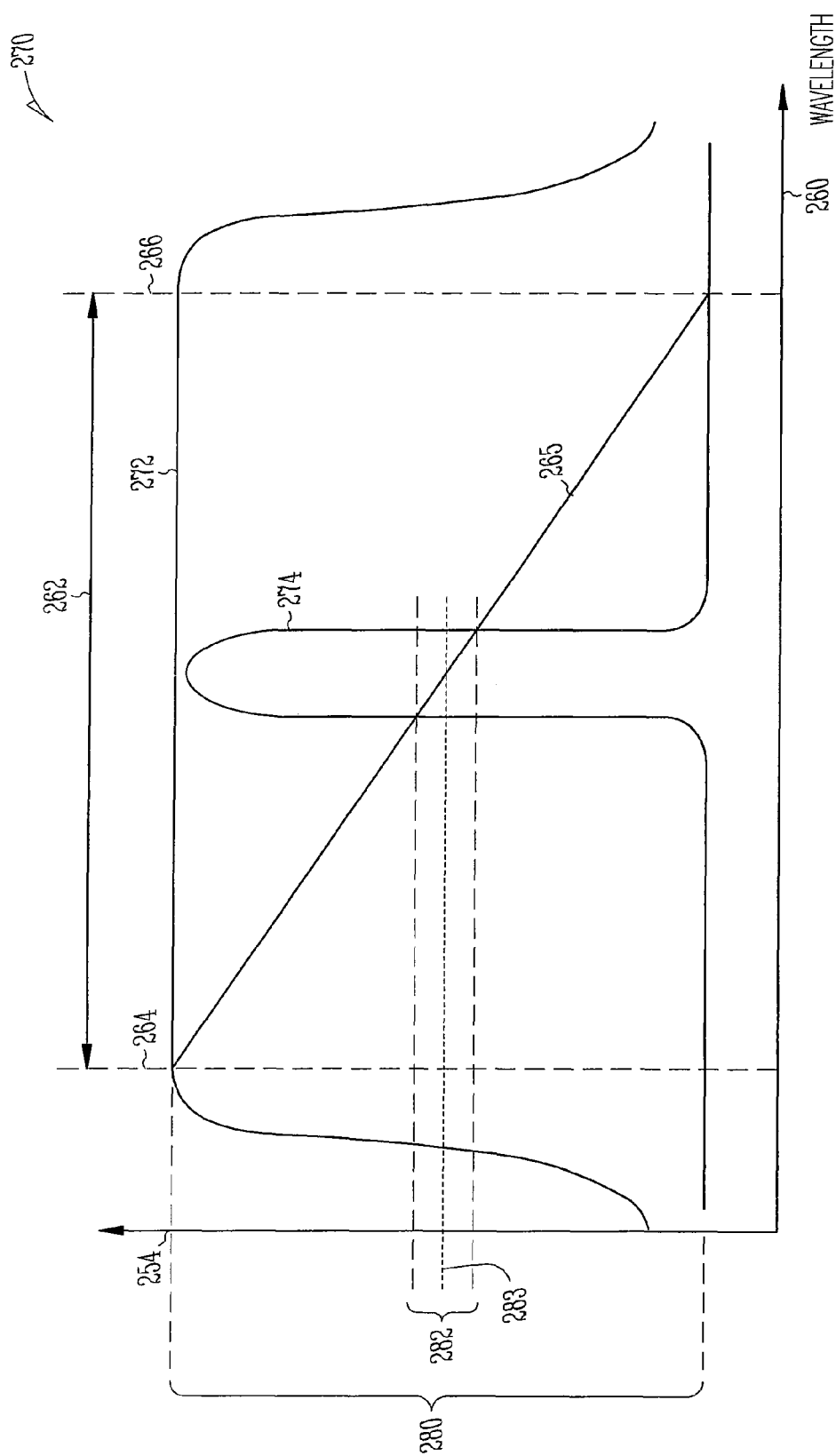
FIG. 2C illustrates a graph of retardation versus wavelength of light according to various embodiments.

FIG. 2C illustrates a graph 270 of retardation for two different ranges of light imposed over the vertical axis 254 representing retardation levels, the horizontal axis 260 representative of wavelength, and the retardation curve 265 of FIG. 2B. Graph 270 includes a white light curve 272 indicative of a true white light having an equal leveled of intensity for all wavelengths of light within in the wavelengths included in range 262, including wavelengths included in the true white light at wavelengths 264 and 266.

In instances where the white light represented by white light curve 272 is passed through the polarization filter, such as polarization filter 200 of FIG. 2A, a retardation response having values over the entire range of retardation response 280 as shown in FIG. 2C would be detected at a pure color detector receiving the light after it had passed through the polarization filter.

Graph 270 includes an illustrative curve 274 indicative of a light having the intensity levels indicative of a light resulting from the light represented by true white light curve 272 being transmitted to a target object, and having the reflected light returned to the color sensor include the wavelengths and intensities as represented by curve 274. By passing the wavelengths and intensities of light received back, as represented by curve 274, through the polarization filter, such a polarization filter 200, a retardation response having values in the range of retardation response 282 as shown in FIG. 2C would be detected by a pure color detector receiving the light after it had passed through the polarization filter. In various embodiments, the range of retardation response 282 is processed to provide a mean value 283 representative of the range of retardation response 282.

By comparing the retardation response 280 representative of the known response for the white light originally transmitted from the color sensor to the retardation response 282 representative of the response received back as light from the target object, a determination can be made as to what color or colors were sensed at the target object as a result of the color sensing operation. The determined color or colors can be further compared to expected or desired values for color or colors in order to provide a status associated with the target object and with the color sensing operation performed on the target object.

In various embodiments, retardation response 282 represents a response for a color or colors having a known range of values. The known range of values for color is not limited to any particular values, and in various embodiments represents color values represented by coordinates associated with a color model. A color model is an abstract mathematical model describing the way colors can be represented as tuples of numbers, typically as three or four values or color components. Illustrative color models include color models based on a CIE XYZ color space, RBG color space, HSV color space, and HLS color space.

Embodiments are not limited to any particular color model or color space, and may incorporate any color models or color spaces. In various embodiments, the mean value 283 is converted to coordinates for a given color model. In various embodiments, and based on these generated coordinates, a determination is made as to whether the response represented by the range of retardation response 283 is the desired or expected color response for a given color sensing operation that resulted from receiving light as represented by curve 274 and generating retardation response 283.

Figure 3A:
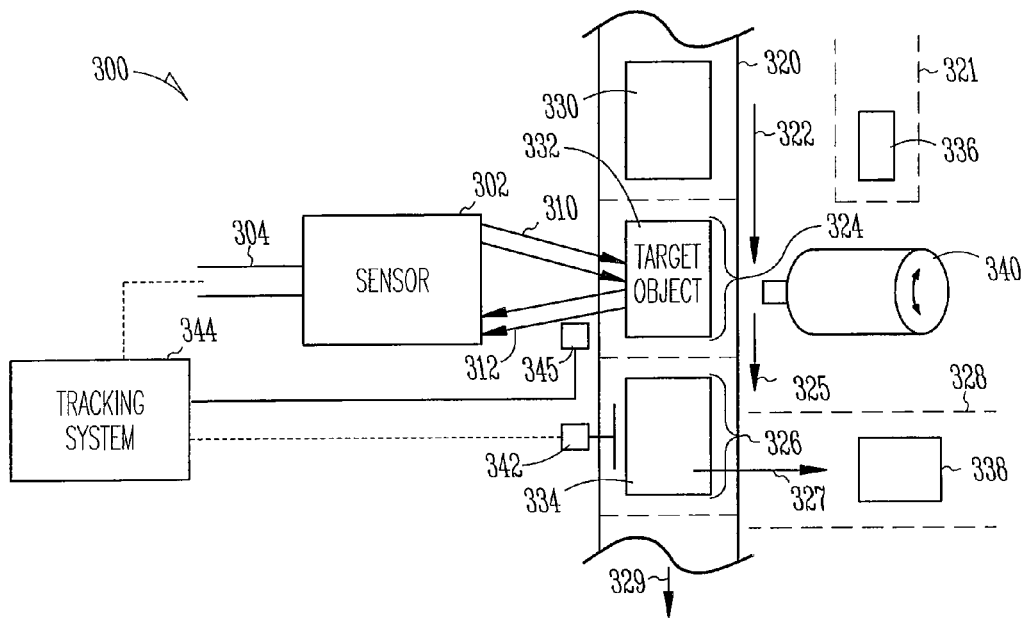
FIG. 3A illustrates a system including a color sensor according to various embodiments.

FIG. 3A illustrates a system 300 including a color sensor 302 according to various embodiments. System 300 includes color sensor 302 located in a position so that color sensor 302 is operable to provide color sensing of target object 332 at a sensing position 324. Target object 332 is not limited to any particular type of object, and includes any object where a color sensing operation on the object is to be performed. Placement of target object 332 into sensing position 324 is not limited to any particular process. In various embodiments, target object 332 is brought into sensing position 324 on a conveyer 320. In various embodiments, target object 332 is initially object 330, and is moved, as represented by arrow 322, into sensing position 324. In various embodiments, target object 332 is brought into sensing position 324 using a pick-and-place 340. In various embodiments, pick-and-place 340 is an industrial robot. In various embodiments, pick-and-place 340 picks up an object 336 from a pick-up position 321, and places object 336 into sensing position 324 for a color sensing operation to be performed on the target object.

In various embodiments, color sensor 302 is coupled to tracking system 344. Tracking system is operable to sense that a target object to be tested is present at sensing position 324, and to trigger color sensor 302 to perform a color sensing operation on target object 332. Sending a target object at sensing position is not limited to any particular sensing device or to any particular means of sensing the target object. Various embodiments include a sensor 345, such as a photocell or a proximity sensor, at sensing position 324 that is operable to detect the presence of a target object 332 at sensing position 324, and to provide an signal to tracking system 344 indicating that a target object 332 is present at tracking position 324.

Various embodiments include determining that a target object is present at sensing position 324 by having the tracking system track a part from an upstream position, such as an upstream position on conveyor 320 as represented by object 330, or a pick-up position, as represented by object 336. In various embodiments, pick-and-place 340 is communicatively coupled to tracking system 344 and is operable to provide a signal indicating that a target object has been placed into sensing position 324. In various embodiments, color sensor 302 is operable to sense the presence of a target object at sensing position 324 by transmitting a light and determining if any light is reflected back from an object at the sensing position 324.

The color sensing operation is represented by arrows 310 and 312, wherein arrows 310 represent a light generated by color sensor 302 and transmitted to target object 332, and arrows 312 represent a portion of the transmitted light that is reflected back and detected by color sensor 302. In various embodiments, color sensor 302 is operable to provide an output signal indicative of a status associated with the color sensing operation performed on target object 332. In various embodiments, the status associated with the color sensing operation performed on target object 332 is either a "pass" indication or a "fail" indication.

In various embodiments, tracking system 344 is operable to move the target object 332 out of the sensing position 324, and to maintain a status provided by the color sensing operation after the color sensing operation is performed on the target object at sensing position 324. In various embodiments, tracking system 344 is operable to move target object 332 along conveyor 320 to pusher 342. In various embodiments, pusher 342 is positioned so at to be operable to push objects, such as object 334, for a pusher position 326 off of conveyor 320 and onto a different conveyor 328. In various embodiments, depending on the status determined by the color sensing operation associated with target object 332, now represented by the object 334 at the position adjacent to pusher 342, tracking system 344 is operable to allow object 334 to continue on conveyor 320, as represented by arrow 329, or to operate pusher 342 to push object 334 off of conveyor 320 and onto conveyer 328, as represented by arrow 327 and object 338. Arrows 329 and 327 represent the divergent flow paths for target objects having different statuses, wherein in various embodiments, arrow 329 represents the path for target objects having a "pass" status, and arrow 327 represents the path for target objects having a "fail" status.

In various embodiments, tracking system 344, based on the status provided by color sensor 302 and associated with target object 332, is operable to allow target object 332 to remain on conveyor 320 and move out of sensing position 324, as represented by arrow 325, or to have pick-and-place 340 pick up target object 332 and move target object 332 to conveyer 328, as represented by object 338.

Figure 3B:
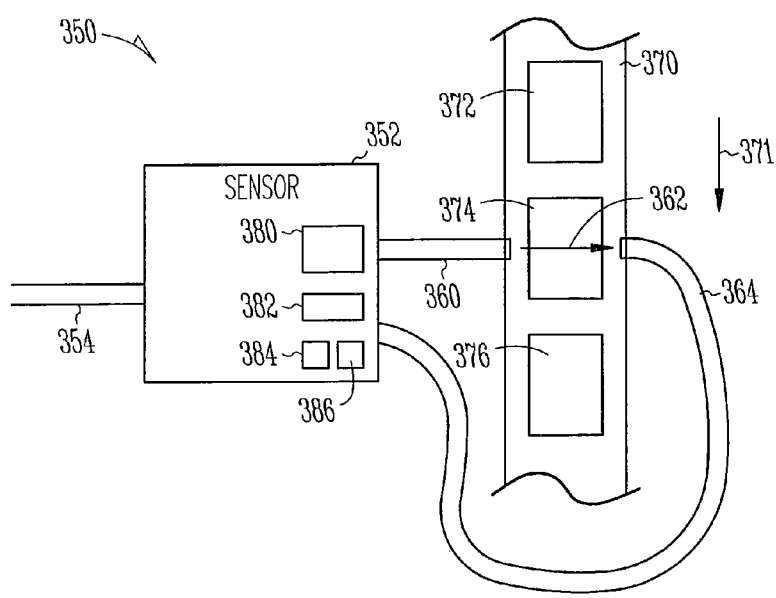
FIG. 3B illustrates a system including a color sensor according to various embodiments.

FIG. 3B illustrates a system 350 including a color sensor 352 according to various embodiments. System 350 includes color sensor 352 located in a position so that color sensor 352 is operable to provide color sensing of target object 374 at a sensing position 362. In various embodiments, system 350 includes a conveyer 370 operable to move objects 372, 374, and 376 into and out of sensing position 362, as represented by arrow 371.

In various embodiments, system 350 includes any of the features described above with respect to a tracking system, including a pusher, and a pick-and-place. In various embodiments, color sensor 352 is coupled to a tracking system, such as tracking system 344, through connection 354. As shown in FIG. 3B, color sensor 352 includes a transmitter 380 operable to generate a light, and to provide the light to a optical cable 360. Optical cable 360 is not limited to any particular type of cable, and includes any type of cable operable to transmit the light generated by transmitter 380. Optical cable 360 provides the light to the sensing position 362. The light at sensing position 362 is transmitted through a translucent or transparent object, such as target object 374 located at sensing position 362, and some portion of the light that passes through target object 374 is received at optical cable 364. Optical cable 364 is operable to return the received light to color sensor 352. At color sensor 352, the received light is provided to first detector 382 without passing through polarization filter 386, and is also provided to a second detector 384 after being passed through polarization filter 386.

Colors sensor 352 process the signals received by detectors 382 and 384 and provides an output status at connections 354.

By using optical cable 360 to transmit light to a target object, and using optical cable 364 to receive the light after the transmitted light from optical cable 360 passes through the target object at the sensing position, system 350 can employ color sensor 352 to perform color sensing operations on translucent and transparent target objects at a sensing position, such as sensing position 362.

Figure 3C:
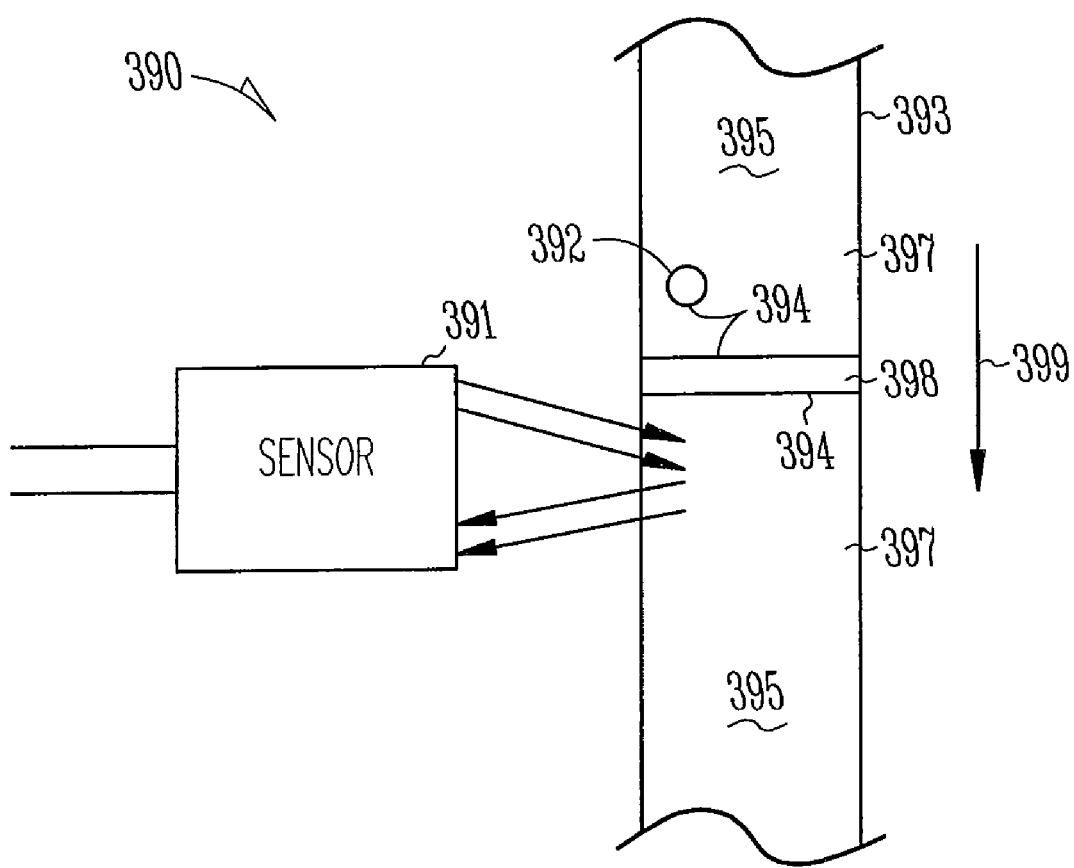
FIG. 3C illustrates a system including a color sensor according to various embodiments.

FIG. 3C illustrates a system 390 including a color sensor 391 according to various embodiments. System 390 includes color sensor 391 located in a position so that color sensor 391 is operable to provide color sensing of target object 393 consisting of a continuous material having one or more color edges 394. In various embodiments, continuous material is not limited to any particular type of material, and includes material formed as rolls, such as paper, fabric material, and metal. In various embodiments, the continuous material has a pattern on a surface 395 of the continuous material that includes a first color 392 adjacent to a second color, such as 397, forming one of the color edges 394. In various embodiments, the color edge 394 is be formed by first color 392 located as an area of color on surface 395 that is different in color for the color or colors of surface 395. In various embodiments, first color 392 is a particular shape, such as but not limited to a circle or a circular area. In various embodiments, the continuous material has a color pattern of a second color 398 on surface 395 adjacent to the first color 397, wherein the second color 398 forms a stripe across continuous material and includes a color different from the adjacent first color 397, thus forming one or more color edges 394.

In operation, the continuous material is moved past color sensor 391, as represented by arrow 399. Color sensor 391 is operable to sample the color of the target object 393 provided as the continuous material moves past color sensor 391. Color sensor 391 is operable to detect the color contrast provided as a color edge on the target object, wherein the color edge is detected due to the color sensor 391 detecting the first color and then detecting the second color adjacent to the first color.

Detecting the color edge is useful in that the color edge in various embodiments determines an edge used to determine where operations, such as cutting operations performed to simulate the continuous material into individual pieces or individual sections, is to be performed. In various embodiments, the color contrast sensing is used to ensure that a desired pattern is repeated at a proper interval along the continuous material. By way of illustration, if the continuous material is moving past color sensor 391 at a known rate, color sensor 391, by taking samples at particular and predetermined times, can be used to determine whether a proper color pattern is consistently present on the continuous material over some given length of the continuous material.

Figure 4:
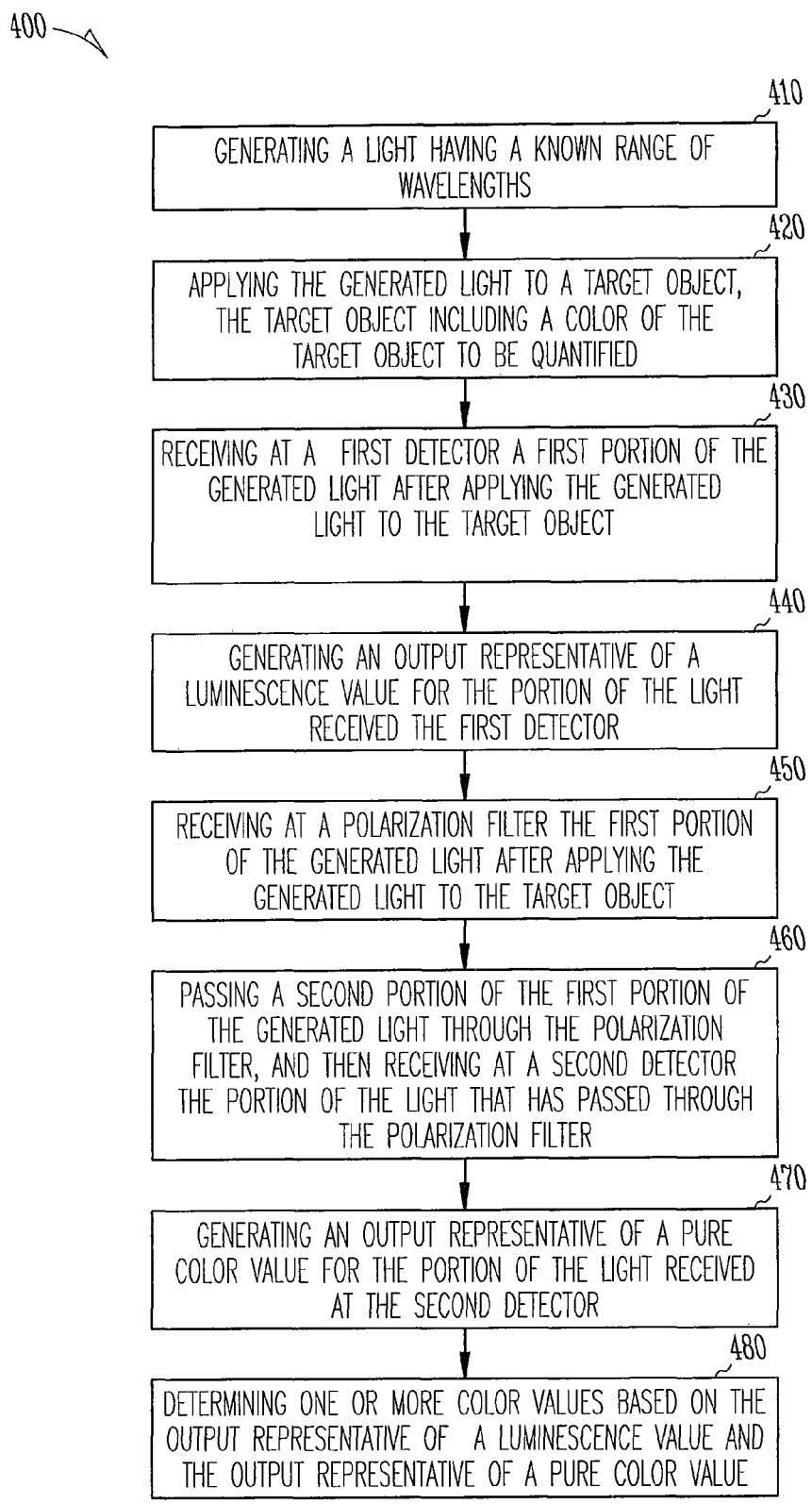
FIG. 4 illustrates a flowchart of one or more methods according to various embodiments of the present inventive subject matter.

FIG. 4 illustrates a flowchart of one or more methods 400 according to various embodiments of the present inventive subject matter.

At block 410, method 400 includes generating a light having a known range of wavelengths.

At block 420, method 400 includes applying the generated light to a target object, the target object including a color of the target object to be quantified.

At block 430, method 400 includes receiving at a first detector a first portion of the generated light after applying the generated light to the target object.

At block 440, method 400 includes generating an output representative of a luminescence value for the portion of the light received at the first detector.

At block 450, method 400 includes receiving at a polarization filter the first portion of the generated light after applying the generated light to the target object.

At block 460, method 400 includes passing a second portion of the first portion of the generated light through the polarization filter, and then receiving at a second detector the portion of the light that has passed through the polarization filter.

In various embodiments, passing the first portion of the generated light through the polarization filter includes passing the light through a first polarizer, then passing the light through a half-wave plate, and then passing the light through a second polarizer, wherein the first polarizer and the second polarizer are arranged as cross polarizer layers.

In various embodiments, passing a second portion of the first portion of the generated light through the polarization filter includes shifting any wavelengths of light included in the portion of light passing through the polarization filter that are outside a given range of wavelengths by more or less than 90 degrees, and attenuated wavelengths passing thorough a second polarizer.

At block 470, method 400 includes generating an output representative of a pure color value for the portion of the light received at the second detector.

At block 480, method 400 includes determining one or more color values based on the output representative of a luminescence value and the output representative of a pure color value. In various embodiments, determining one or more color values further includes comparing the one or more color values to a known or desired color value or a know or desired set of color values to determine if the one or more determined color values based on the output representative of a luminescence value and the output representative of a pure color value are the same as the known or desired color value or color values.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments, and other embodiments, will be apparent to those of skill in the art upon studying the above description.

What is claimed is:

1. An apparatus including:
   a color sensor including a transmitter portion and a receiver portion;
   the transmitter portion including a light source operable to generate and transmit a light having a particular range of wavelengths;
   the receiver portion including a first detector operable to receive a first portion of the light emitted from the transmitter portion and to measure a luminance of the received first portion of the emitted light; and
   a second detector including a polarization filter, the second detector operable to receive a second portion of the light emitted from the transmitter after the second portion has passed through the polarization filter, and operable to measure a pure color of the received second portion of transmitted light.

2. The apparatus of claim 1, wherein the polarization filter includes a half-wave plate located between two crossed polarizer layers.

3. The apparatus of claim 2, wherein the half-wave plate is a wavelength dependent structure designed for a specific wavelength matching the particular range of wavelengths generated by the transmitter portion.

4. The apparatus of claim 1, wherein the color sensor includes a signal processing module including a first input to receive an output from the first detector and a second input to receive an output from the second detector, and operable to provide an output signal having a value dependent on a ratio of the output from the first detector and the output from the second detector.

5. The apparatus of claim 1, further including one or more tables storing values for at least one set of color coordinates.

6. The apparatus of claim 1, wherein the light source is a light emitting diode operable to emit a white light including light having wavelengths of light over a range of visible light.

7. The apparatus of claim 1, wherein the light source is a light emitting diode operable to emit light within a range of ultraviolet wavelengths.

8. The apparatus of claim 1, wherein the light source is a light emitting diode operable to emit light within a range of infrared wavelengths.

9. The apparatus of claim 1, wherein the polarization filter is a thin film based polarization filter.

10. The apparatus of claim 1, wherein the polarization filter is a plasmonic based polarization filter.

11. The apparatus of claim 1, wherein the polarization filter is a resonant based polarization filter.

12. The apparatus of claim 1, wherein the polarization filter is a dye based polarization filter.

13. The apparatus of claim 1, wherein the polarization filter is a sub-wavelength grating based polarization filter.

14. A method comprising:
generating a light having a known range of wavelengths;
applying the generated light to a target object, the target object including a color of the target object to be quantified;
receiving at a first detector a first portion of the generated light after applying the generated light to the target object;
generating an output representative of a luminescence value of the portion of the light received at the first detector;
receiving at a polarization filter the first portion of the generated light after applying the generated light to the target object;
passing a second portion of the first portion of the generated light through the polarization filter, and then receiving at a second detector the portion of the light that has passed through the polarization filter; and
generating an output representative of a pure color value for the portion of the light received at the second detector.

15. The method of claim 14, wherein passing the first portion of the generated light through the polarization filter includes passing the light through a first polarizer, then passing the light through a half-wave plate, and then passing the light through a second polarizer, wherein the first polarizer and the second polarizer are arranged as cross polarizer layers.

16. The method of claim 14, wherein passing a second portion of the first portion of the generated light through the polarization filter includes shifting any wavelengths of light included in the portion of light passing through the polarization filter that are outside of a given range of wavelengths by more or less than 90 degrees, and attenuated wavelengths passing through a second polarizer.

17. A system comprising:
a color sensor including a transmitter portion and a receiver portion, wherein the transmitter portion including a light source operable to emit a light having a particular range of wavelengths, the receiver portion including a first detector operable to receive a reflected portion of the light emitted from the transmitter portion after the emitted light is reflected off a surface of a target object, and to measure a luminance of the received reflected portion of the emitted light, and a second detector including a color-specific filter, the second detector operable to receive the reflected portion of the light emitted from the portion of the light emitted from a the transmitter portion after the second portion has passed through the color specific filter, and operable to measure a pure color of the received second portion of emitted light;
a sensing position located proximal to the color sensor and at a distance from the color sensor wherein the transmitter portion is operable to transmit a light from the light source and have the transmitted light incident on an object present at the sensing position and wherein the light incident on the object reflects off a surface of the object to generate the reflected portion of the light; and
a mechanism operable to place the object into the sensing position and to remove the object from the sensing position.

18. The system of claim 17, wherein the sensing position includes a sensor to determine that a target object is present at the sensing position and to provide a signal to a tracking system indicative that the target object is present at the sensing position.

19. The system of claim 17, wherein the color system is operable to detect a color edge on a target object, wherein the color edge includes an edge formed by a first color adjacent to a second color on a surface of the target object.

20. The system of claim 17, wherein the color sensor includes an output operable to provide a first signal indicative that a test of color has been completed on a target object, and a second signal indicative of whether the test resulted in a passed or in a failed status.

* * * * *